(12) United States Patent
Shimoe et al.

(10) Patent No.: US 8,109,915 B2
(45) Date of Patent: Feb. 7, 2012

(54) PULL-ON DISPOSABLE WEARING ARTICLE

(75) Inventors: Nariaki Shimoe, Kagawa-ken (JP);
Toshifumi Otsubo, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 1231 days.

(21) Appl. No.: 11/457,356

(22) Filed: Jul. 13, 2006

(65) Prior Publication Data
US 2006/0282054 A1 Dec. 14, 2006

Related U.S. Application Data

(63) Continuation-in-part of application No. 11/056,284, filed on Feb. 14, 2005, now abandoned, which is a continuation of application No. PCT/JP03/010667, filed on Aug. 22, 2003.

(30) Foreign Application Priority Data

Aug. 30, 2002 (JP) ................................ 2002-255672

(51) Int. Cl.
*A61F 13/20* (2006.01)
(52) U.S. Cl. ............. 604/385.23; 604/385.24; 604/393; 604/394; 604/395; 604/396; 604/385.22
(58) Field of Classification Search .. 604/385.24–385.3, 604/393–396, 385.22
See application file for complete search history.

(56) References Cited

U.S. PATENT DOCUMENTS

| | | |
|---|---|---|
| 5,171,239 A | 12/1992 | Igaue et al. |
| 5,415,649 A | 5/1995 | Watanabe et al. |
| 5,575,783 A | 11/1996 | Clear et al. |
| 5,745,922 A | 5/1998 | Rajala et al. |
| 5,846,232 A | 12/1998 | Serbiak et al. |
| 6,045,543 A | 4/2000 | Pozniak et al. |
| 6,049,916 A | 4/2000 | Rajala et al. |
| 6,297,424 B1 | 10/2001 | Olson et al. |
| 6,595,976 B2 | 7/2003 | Shimoe et al. |
| 6,602,238 B2 * | 8/2003 | Takei et al. ............... 604/385.26 |
| 6,923,797 B2 | 8/2005 | Shinohara et al. |
| 7,217,261 B2 * | 5/2007 | Otsubo et al. ............ 604/385.29 |
| 2002/0049421 A1 | 4/2002 | Hayase et al. |
| 2004/0167494 A1 * | 8/2004 | Otsubo ..................... 604/385.27 |

FOREIGN PATENT DOCUMENTS

EP 761193 B1 3/1997

(Continued)

OTHER PUBLICATIONS

Abstract of JP Publication No. 2001-231078.

(Continued)

*Primary Examiner* — Tatyana Zalukaeva
(74) *Attorney, Agent, or Firm* — Lowe, Hauptman, Ham & Berner, LLP

(57) ABSTRACT

A pull-on disposable wearing article has a base sheet including an inner sheet and an outer sheet. A plurality of auxiliary elastic members extending across a panel are interposed between the inner sheet and the outer sheet and attached to these sheets between waist surrounding elastic members and leg-holes so that these auxiliary elastic members may contract in the waist-circumferential direction. Each of the auxiliary elastic members has transversely opposite end portions secured to the inner and outer sheets and an intermediate portion not directly bonded to the inner and outer sheets.

5 Claims, 9 Drawing Sheets

FOREIGN PATENT DOCUMENTS

| | | |
|---|---|---|
| EP | 0761194 | 3/1997 |
| EP | 0762293 | 3/1997 |
| EP | 0990434 | 4/2000 |
| EP | 1157681 | 11/2001 |
| EP | 1184012 | 3/2002 |
| EP | 1197195 | 4/2002 |
| JP | 08-084747 | 4/1996 |
| JP | 1997-38134 | 2/1997 |
| JP | 09-056747 | 3/1997 |
| JP | 09-099006 | 4/1997 |
| JP | 11-299829 | 11/1999 |
| JP | 2000-107225 | 4/2000 |
| JP | 2001-145666 | 5/2001 |
| JP | 2001-157690 | 6/2001 |
| JP | 2002-095692 | 4/2002 |
| JP | 2003-038556 | 2/2003 |

OTHER PUBLICATIONS

Abstract of EP Patent No. 0761193 A2.

* cited by examiner

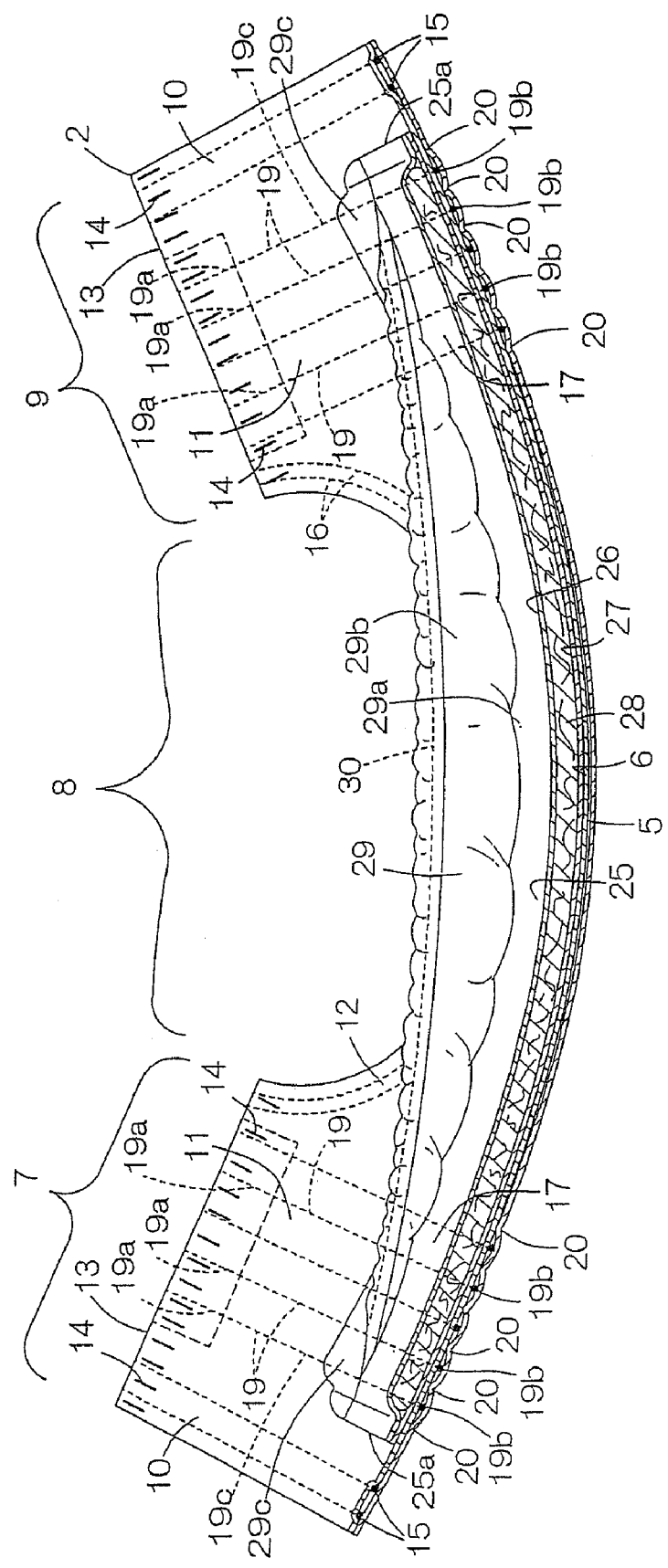

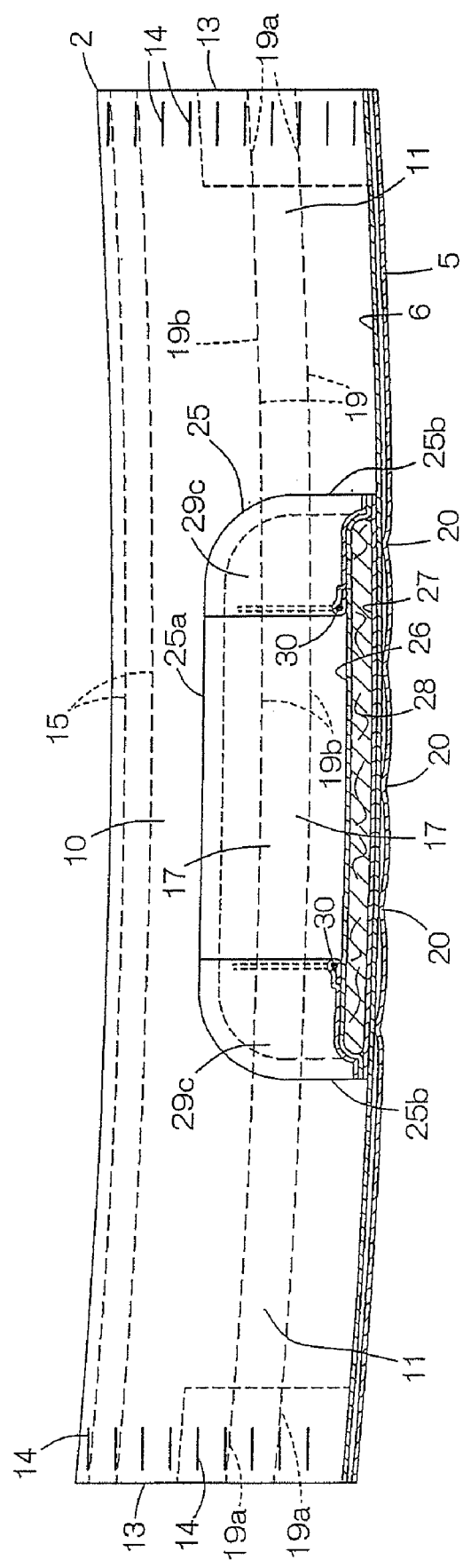

PULL-ON DISPOSABLE WEARING ARTICLE

RELATED APPLICATIONS

This application is a continuation in part of Ser. No. 11/056,284, filed Feb. 14, 2005 which claims priority from PCT/JP03/010667, filed Aug. 22, 2003, and JP 2002-255672, filed Aug. 30, 2002. The above-listed applications are incorporated by reference herein in their entirety.

BACKGROUND OF THE INVENTION

The present invention relates to a pull-on disposable wearing article for absorption and containment of bodily discharges.

Japanese Patent Application Publication No. 1997-56747A discloses a pull-on disposable wearing article comprising a liquid-pervious topsheet facing a wearer's body, a liquid-impervious backsheet facing away from the wearer's body and a liquid-absorbent core interposed between these top- and backsheets wherein front and rear waist regions are connected to each other in vicinities of lateral margins of waist's opposite lateral zones by means of a plurality of heat-sealing spots intermittently arranged in a longitudinal direction so as to form a waist-hole and a pair of leg-holes.

This wearing article is provided with a plurality of waist surroundable elastic members extending in a waist circumferential direction and attached to a waist's upper end portion in the front waist region so as to be contractible in a waist-circumferential direction. Between the waist surroundable elastic members and the leg-holes, the wearing article is further provided with a plurality of auxiliary elastic members extending in the waist-circumferential direction so as to be contractible in the waist-circumferential direction. The peripheral portions of the leg-holes are also provided with a plurality of leg surroundable elastic members, respectively, so as to be contractible in the leg-circumferential direction.

The waist surroundable elastic members and the leg surroundable elastic members are interposed between the tops- and the backsheets and bonded to respective inner surfaces of these sheets by means of hot melt adhesive. Transversely opposite lateral zones of the respective auxiliary elastic members are also interposed between the top and back sheet and secured to the inner surfaces of these sheets by means of a hot melt adhesive. Intermediate portions of the respective auxiliary elastic members extending across the core are interposed between the backsheet and the core and secured to the backsheet by means of a hot melt adhesive.

This wearing article has advantageous effects that a distance by which each pair of the adjacent auxiliary elastic members are spaced apart from each other is smaller in the vicinities of the longitudinally opposite ends of the core than in the other zone. Such a unique arrangement is effective to keep the wearing article in close contact with the wearer's waist in the vicinities of the longitudinally opposite ends of the core and thereby to prevent leakage of bodily discharges from occurring in the vicinities of the ends of the core.

In the wearing article disclosed in the above-cited Publication, the auxiliary elastic members are secured to the top and back sheets while these elastic members are stretched in the waist-circumferential direction at a predetermined stretching ratio, so contraction of the auxiliary elastic members in the waist-circumferential direction causes the top and back sheet also to contract inward in the waist-circumferential direction. In this article, however, each of the auxiliary elastic members having been stretched can not restore its initial non-stretched dimension although these auxiliary elastic members contract inward in the waist-circumferential direction because contraction of the auxiliary elastic members is restricted by the presence of adhesive. Thus the regions of the top and back sheets having the auxiliary elastic members therein are stretchable and contractible within a substantially narrower range than the range within which the auxiliary elastic members themselves are stretchable and contractible. This means that the range within which the auxiliary elastic members are stretchable and contractible can not be effectively utilized.

SUMMARY OF THE INVENTION

It is an object of the invention to provide a pull-on disposable wearing article improved so that the region of the article having the auxiliary elastic members therein may be stretchable and contractible within a substantially same range as the range within which the auxiliary elastic members themselves are stretchable and contractible.

An embodiment includes a pull-on disposable wearing article, comprising: a base sheet defining a front waist region, a rear waist region and a crotch region extending between the front and rear waist regions; a liquid-absorbent panel attached to an inner side of the base sheet so as to extend over the crotch region further into the front and rear waist regions;

the base sheet having waist surrounding upper end portions lying outside longitudinally opposite ends of the panel and transversely opposite lateral zones lying outside transversely opposite side edges of the panel, wherein the transversely opposite lateral zones are connected to each other at bonding sites disposed longitudinally along lateral margins of the transversely opposite lateral zones to define a waist-hole and a pair of leg-holes; waist surrounding elastic members extending in a waist-circumferential direction along the waist surrounding upper end portions; a plurality of auxiliary elastic members located between the waist surrounding elastic members and the leg-holes in at least one of the front and rear waist regions, each of the auxiliary elastic members having a working section extending in the waist-circumferential direction between inner ends of the bonding sites. When each of the auxiliary elastic members is in a relaxed, non-stretched state and is not attached to the base sheet, the working section of the auxiliary elastic member has a first dimension. The panel in the at least one of the front and rear waist regions has a second dimension as measured in the waist-circumferential direction. The first dimension is substantially equal to or longer than the second dimension. The base sheet has a region coextensive, in the waist-circumferential direction, with the working sections of the auxiliary elastic members, the region also extending between the inner ends of the bonding sites. When the auxiliary elastic members are in a non-stretched state and remain attached to the base sheet, the region of the base sheet has a third dimension in the waist-circumferential direction. A ratio of the third dimension to the first dimension is in a range of 1.0 to 1.1.

A further embodiment includes a disposable wearing article, comprising a base sheet defining front waist region, a rear waist regions and a crotch region extending between the front and rear waist regions; a liquid-absorbent panel attached to an inner side of the base sheet so as to extend over the crotch region further into the front and rear waist regions; the base sheet further having waist surrounding upper end portions lying outside longitudinally opposite ends of the panel and transversely opposite lateral zones lying outside transversely opposite side edges of the panel; waist surrounding elastic members extending in a waist-circumferential direction along the waist surrounding upper end portions; leg-surrounding elastic members extending along the transversely opposite lateral zones in the crotch region; a plurality of auxiliary elastic members located between the waist surrounding elastic members and the leg-surrounding elastic members in at least one of the front and rear waist regions, and extending in the waist-circumferential direction between lateral margins of the transversely opposite lateral zones; each of the auxiliary elastic members having longitudinal opposite end portions secured to the base sheet in vicinities of the lateral margins of the transversely opposite lateral zones, and an intermediate portion extending between the opposite end portions. When each of the auxiliary elastic members is in a relaxed, non-stretched state and is not attached to the base sheet, the auxiliary elastic member has a first dimension. The panel in the at least one of the front and rear waist regions has a second dimension as measured in the waist-circumferential direction. The first dimension is substantially equal to or longer than the second dimension. The base sheet has a region coextensive, in the waist-circumferential direction, with the auxiliary elastic members, the region also extending between the lateral margins of the transversely opposite lateral zones. When the auxiliary elastic members are in a non-stretched state and remain attached to the base sheet, the region of the base sheet has a third dimension in the waist-circumferential direction. A ratio of the third dimension to the first dimension is in a range of 1.0 to 1.1.

A further embodiment includes a pull-on disposable wearing article, comprising: a base sheet defining a front waist region, a rear waist region and a crotch region extending between said front and rear waist regions; a liquid-absorbent panel attached to an inner side of said base sheet so as to extend over said crotch region and into said front and rear waist regions; said base sheet having waist surrounding upper end portions lying outside longitudinally opposite ends of said panel and transversely opposite lateral zones lying outside transversely opposite side edges of said panel, wherein said transversely opposite lateral zones are connected to each other at bonding sites disposed longitudinally along lateral margins of said transversely opposite lateral zones to define a waist-hole and a pair of leg-holes; waist surrounding elastic members extending in a waist-circumferential direction along said waist surrounding upper end portions; a plurality of auxiliary elastic members located between said waist surrounding elastic members and said leg-holes in at least one of said front and rear waist regions, each of said auxiliary elastic members having a working section extending in the waist-circumferential direction between inner ends of the bonding sites. When each of said auxiliary elastic members is in a relaxed, non-stretched state and is not attached to said base sheet, the working section of said auxiliary elastic member has a first dimension as measured in said waist-circumferential direction. Said panel in said at least one of said front and rear waist regions has a second dimension as measured in said waist-circumferential direction between said transversely opposite side edges of said panel. Said first dimension is substantially equal to or longer than said second dimension. Said base sheet has a region coextensive, in the waist-circumferential direction, with the working sections of said auxiliary elastic members, said region also extending between the inner ends of said bonding sites. When said auxiliary elastic members are in a non-stretched state and remain attached to said base sheet, said region of said base sheet has a third dimension in the waist-circumferential direction. A ratio of the third dimension to the first dimension is in a range of 1.0 to 1.1.

In a further embodiment, said base sheet comprises first and second sheets joined to each other, and each of said auxiliary elastic members is positioned between said first and second sheets and has (i) longitudinal opposite end portions lying in vicinities of said lateral margins of said transversely opposite lateral zones and secured to at least one of said first and second sheets of said base sheet, and (ii) an intermediate portion contiguous to, extending between and connecting said opposite end portions, said intermediate portion being directly bonded neither to the first sheet nor to the second sheet of said base sheet and defining said working portion.

Another embodiment further comprises a plurality of joining spots joining said first and second sheets together, wherein at least one of said joining spots is positioned between each pair of adjacent said auxiliary elastic members; and all said joining spots are positioned between said transversely opposite side edges of said panel.

A further embodiment includes a disposable wearing article, comprising: abase sheet defining a front waist region, a rear waist region and a crotch region extending between said front and rear waist regions; a liquid-absorbent panel attached to an inner side of said base sheet so as to extend over said crotch region and into said front and rear waist regions; said base sheet further having waist surrounding upper end portions lying outside longitudinally opposite ends of said panel and transversely opposite lateral zones lying outside transversely opposite side edges of said panel; waist surrounding elastic members extending in a waist-circumferential direction along said waist surrounding upper end portions; leg-surrounding elastic members extending along the transversely opposite lateral zones in said crotch region; a plurality of auxiliary elastic members located between said waist surrounding elastic members and said leg-surrounding elastic members in at least one of said front and rear waist regions, and extending in said waist-circumferential direction between lateral margins of said transversely opposite lateral zones; each of said auxiliary elastic members having longitudinal opposite end portions secured to said base sheet in vicinities of said lateral margins of said transversely opposite lateral zones, and an intermediate portion extending between said opposite end portions. When each of said auxiliary elastic members is in a relaxed, non-stretched state and is not attached to said base sheet, said auxiliary elastic member has a first dimension. Said panel in said at least one of said front and rear waist regions has a second dimension as measured in said waist-circumferential direction. Said first dimension is substantially equal to or longer than said second dimension; said base sheet has a region coextensive, in the waist-circumferential direction, with said auxiliary elastic members, said region also extending between the lateral margins of said transversely opposite lateral zones. When said auxiliary elastic members are in a non-stretched state and remain attached to said base sheet, said region of said base sheet has a third dimension in the waist-circumferential direction. A ratio of the third dimension to the first dimension is in a range of 1.0 to 1.1.

In a further embodiment, said base sheet comprises first and second sheets joined to each other, and each of said auxiliary elastic members is positioned between said first and second sheets and has (i) the longitudinal opposite end portions secured to at least one of said first and second sheets of said base sheet, and (ii) the intermediate portion being directly bonded neither to the first sheet nor to the second sheet of said base sheet.

Another embodiment further comprises a plurality of joining spots joining said first and second sheets together, wherein at least one of said joining spots is positioned between each pair of adjacent said auxiliary elastic members; and all said joining spots are positioned between said transversely opposite side edges of said panel.

BRIEF DESCRIPTION OF THE DRAWINGS

FIG. 3 is a sectional view taken along a line I-I in FIG. 2;

FIG. 4 is a sectional view taken along a line II-II in FIG. 2;

DETAILED DESCRIPTION OF THE PREFERRED EMBODIMENTS

Detail of the pull-on disposable wearing article according to the present invention will be more fully understood from the description given hereunder with reference to the accompanying drawings.

Figure 1:
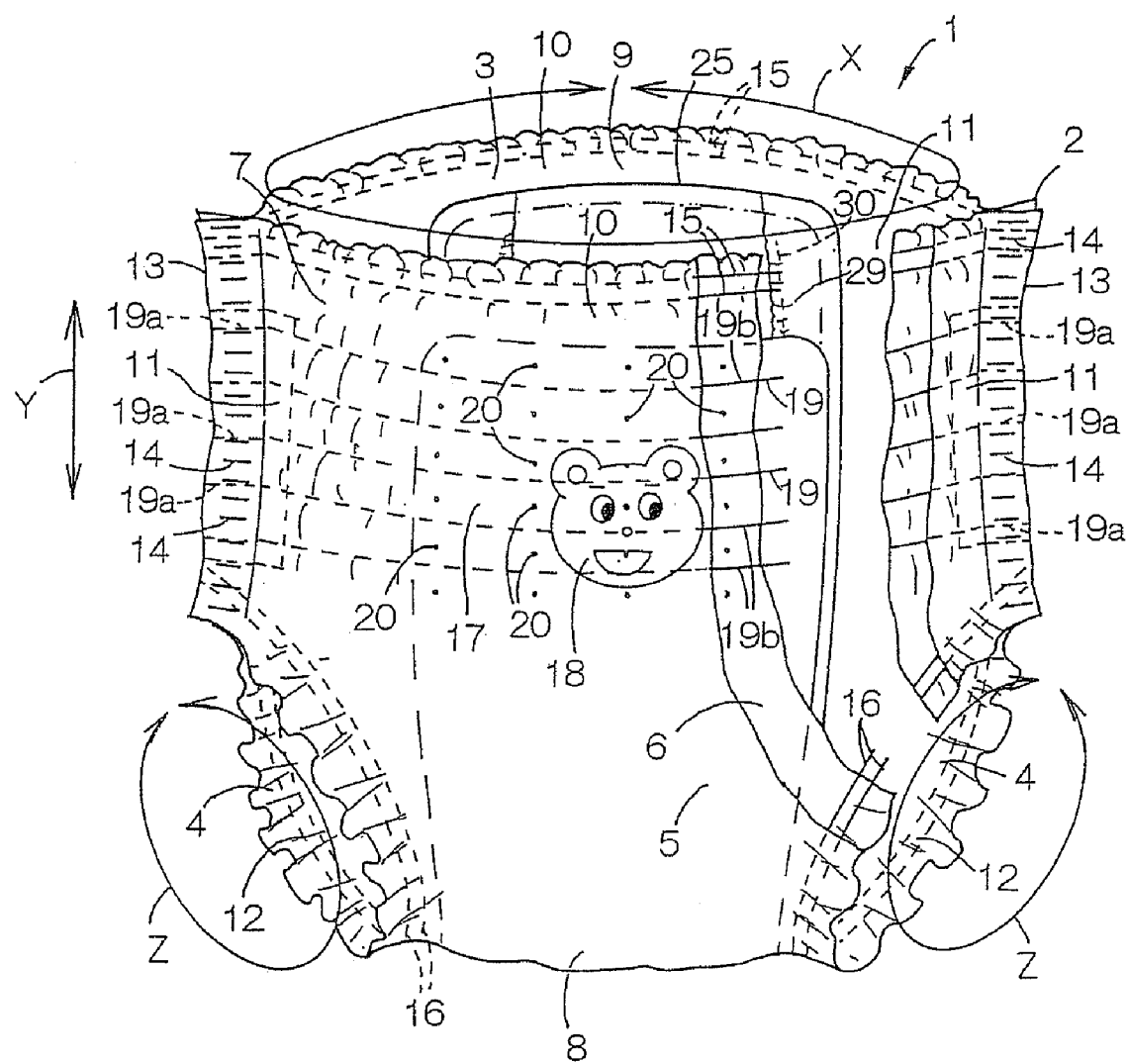
FIG. 1 is a partially cutaway perspective view showing a disposable wearing article according to the invention.
Figure 2:
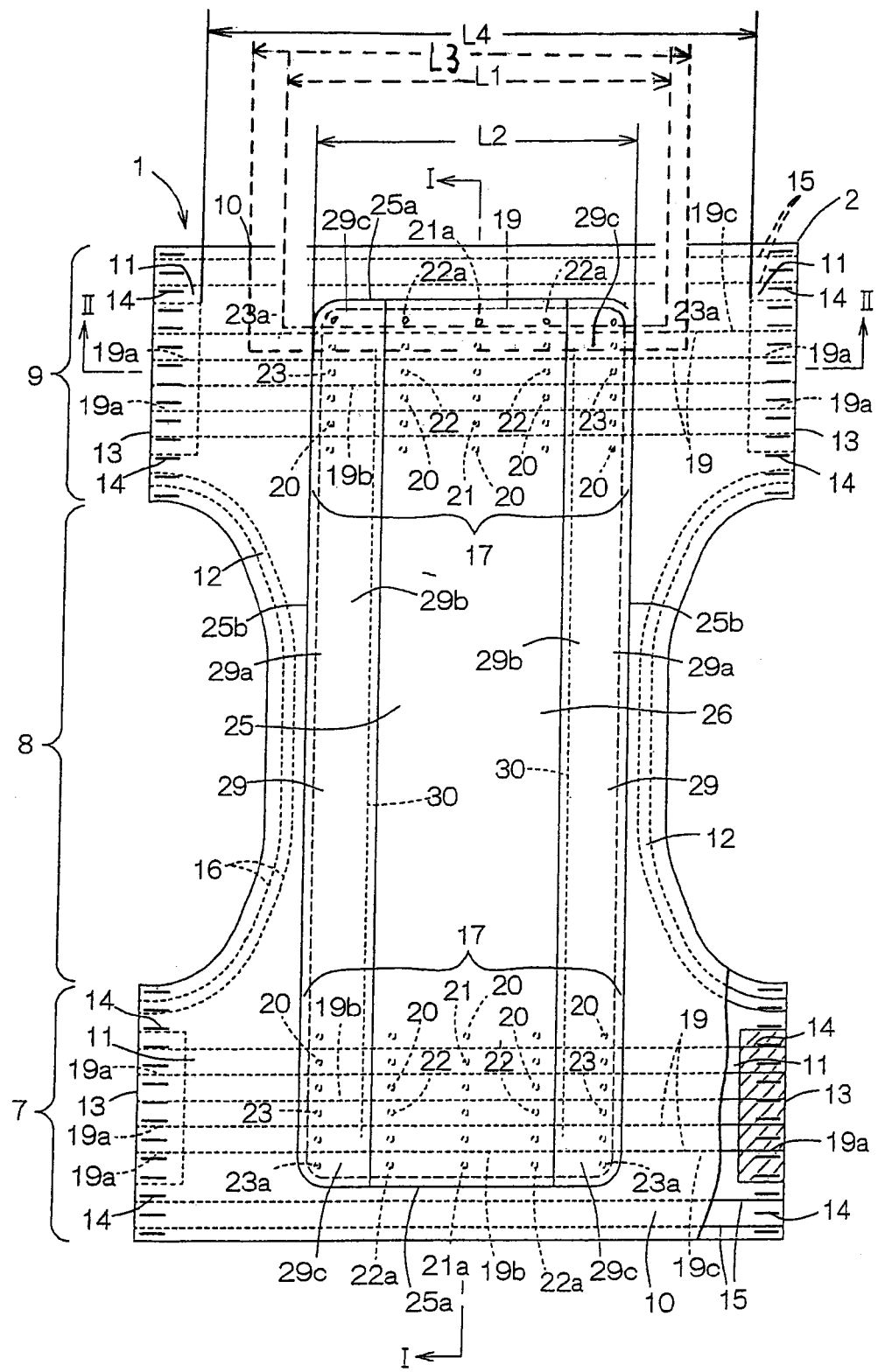
FIG. 2 is a developed plan view showing the article of FIG. 1 with the front and rear waist regions disconnected from each other and in a state where the article is stretched in a transverse direction.
Figure 2A:
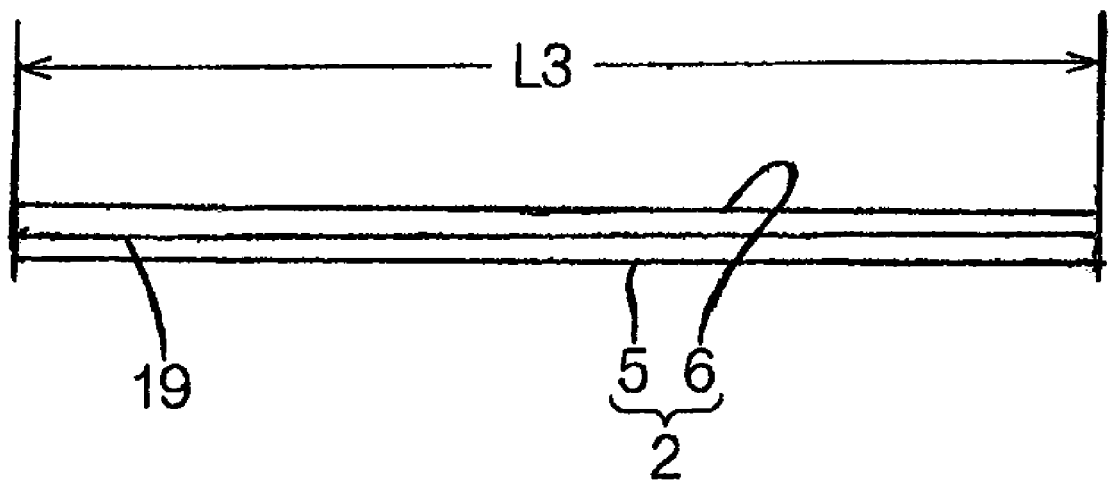
FIG. 2A is a schematically sectional view showing dimension L3 of the base sheet when the auxiliary elastic members are in a non-stretched state but remaining attached to the base sheet.

FIG. 1 is a partially cutaway perspective view showing a pull-on wearing article 1 according to a typical embodiment of the invention, FIG. 2 is a developed plan view showing the article 1 of FIG. 1 with front and rear waist regions disconnected from each other along transversely opposite lateral zones 11 and in a state where the article is stretched in a transverse direction, FIG. 2A is a schematically sectional view showing dimension L3 of the base sheet when the auxiliary elastic members are in a non-stretched state but remaining attached to the base sheet, FIG. 3 is a sectional view taken along a line I-I in FIG. 2, showing the article 1 slightly curved and FIG. 4 is a sectional view taken along a line II-II in FIG. 2. In FIG. 1, a waist-circumferential direction is indicated by an arrow X, a longitudinal direction is indicated by an arrow Y and a leg-circumferential direction is indicated by an arrow Z. In FIG. 2, chain double-dashed lines indicate an auxiliary elastic member 19 in a non-stretched state. Expression "inner surfaces of an inner sheet 6 (first sheet) and an outer sheet 5 (second sheet)" should be understood to be surfaces facing a panel 25 and expression "outer surfaces of these sheets 5, 6" should be understood to be surfaces facing away from the panel 25.

The article 1 comprises a base sheet 2 and the liquid-absorbent panel 25 attached to an inner side of the base sheet 2. The panel 25 is smaller than the base sheet 2 in both longitudinal and transverse dimensions. The article 1 has a waist-hole 3 and a pair of leg-holes 4.

The base sheet 2 comprises the inner sheet 6 (first sheet) lying aside of the panel 25 and the outer sheet 5 (second sheet) lying outside the inner sheet 6. The base sheet 2 defines front and rear waist regions 7, 9 opposed to each other and a crotch region 8 extending between these waist regions 7, 9.

The base sheet 2 has a waist surrounding end portion 10 extending in the waist-circumferential direction outside longitudinally opposite ends 25a of the panel 25, the transversely opposite lateral zones 11 extending in the longitudinal direction outside transversely opposite side edges 25b of the panel 25 and peripheral edge portions 12 of the respective leg-holes 4 extending in the leg-circumferential direction outside the side edges 25b of the panel 25. In the base sheet 2, lateral margins 13 of the respective transversely lateral zones 11 are overlaid and joined together by means of a plurality of heat-sealing sites 14 intermittently arranged in the longitudinal direction in vicinities of the respective lateral margins 13.

Along the waist surrounding upper end portion 10, in the vicinities of the lateral margins 13 of the respective transversely opposite lateral zones 11 and along peripheral edge portions 12 of the respective leg-holes 4, the inner and outer sheets 6, 5 are overlaid together and these sheets 5, 6 having respective inner surfaces joined together. The waist surrounding upper end portion 10 is provided with a plurality of waist surrounding elastic members 15 so as to be contractible in the waist-circumferential direction. The waist surrounding upper end portion 10 is formed with a plurality of gathers as the waist surrounding elastic members 15 contract in the waist-circumferential direction. The peripheral edge portions 12 of the leg-holes 4 are provided with a plurality of leg surrounding elastic members 16 so as to be contractible in the leg-circumferential direction. The peripheral edge portions 12 of the leg-holes 4 are formed with a plurality of gathers as these leg surrounding elastic members 16 contract in the leg-circumferential direction. The waist surrounding elastic members 15 and the leg surrounding elastic members 16 are interposed between the inner sheet 6 and the outer sheet 5 and secured to these sheets 5, 6.

In the front waist region 7, a zone 17 of the outer sheet 5 occupied by the panel 25 is provided with an illustration of bear cub 18 (indication element). This illustration is printed on the outer surface of the outer sheet 5. So far as being recognizable from outside, it is possible to print the illustration 18 on the inner surface of the outer sheet 5 and it is also possible to print the illustration 18 either on the inner surface or on the outer surface of the inner sheet 6. The front and rear waist regions 7, 9 are provided with a plurality of auxiliary elastic members 19 extending across the panel 25 in the waist-circumferential direction so as to be contractible in the waist-circumferential direction.

The auxiliary elastic members 19 are interposed between the inner sheet 6 and the outer sheet 5 and spaced apart from one another by a given dimension in the longitudinal direction between the waist surrounding elastic members 15 and the leg-holes 4. Each of the auxiliary elastic members 19 has transversely opposite end portions 19a lying on the lateral margins 13 of the respective transversely opposite lateral zones 11 of the base sheet 2 and secured to at least one, preferably both, of the inner sheet 6 and the outer sheet 5, and an intermediate portion 19b lying between and connecting the opposite end portions 19a. The intermediate portion 19b is directly secured neither to the inner sheet 6 nor to the outer sheet 5.

Each of the auxiliary elastic members 19 is attached to the base sheet 2 and has a working section which is located laterally inboard of the heat-sealing sites 14, and opposite non-working sections which are coextensive with or located laterally outboard of the heat-sealing sites 14. It should be noted that the working section is not necessarily the same as the intermediate portion 19b and may include, e.g., parts of the end portions 19a in addition to the intermediate portion 19b. In this particular embodiment, the intermediate portion 19b defines the working section and the end portions 19a define the non-working sections respectively.

As best seen in FIG. 2, the working sections of the auxiliary elastic members 19, when said auxiliary elastic members 19 are in a stretched state, have dimension L4 in the waist-circumferential direction.

The working section of each of auxiliary elastic members 19 further has a relaxed or natural dimension L1 (also in the waist-circumferential direction) when said working section is in a relaxed, non-stretched state and is not attached to the base sheet 2.

The base sheet 2 has a region which is coextensive with the working sections of the auxiliary elastic members 19 and, therefore, also located laterally inboard of the heat-sealing sites 14. Thus, in the diaper of FIG. 1-4 where the auxiliary elastic members are attached to the base sheet 2, the region of the base sheet 2 and the working sections of auxiliary elastic members 19 always have the same dimension. For example, when the auxiliary elastic members 19 are in the stretched state as shown in FIG. 2, the region of the base sheet also has dimension L4 like the working sections of the auxiliary elastic members 19.

However, when the auxiliary elastic members 19 are in a non-stretched state but remain attached to the base sheet, their working sections and the region of said base sheet 2 contract to have the same dimension L3 which is equal to or slightly greater than relaxed or natural dimension L1 of the working sections. In FIGS. 2A and 3, the non-stretched state of the region of said based sheet 2 (which still remains attached to the auxiliary elastic members) is illustrated by way of the wavy line associated with dimension indicator L3.

FIG. 2 further indicates that the panel 25 has a dimension L2 in the waist-circumferential direction.

It should be noted that the reason why the relaxed or natural dimension L1 of the working sections of auxiliary elastic members 19 are shown in FIG. 2, despite the fact that FIG. 2 shows the article 1 stretched in the transverse direction, is that the indication of the dimension L1 in FIG. 2 facilitates visual recognition of a dimension interrelationship among the dimensions L1, L2, L3 and L4. The dimension L3 of the region of the base sheet 2 and the working sections of auxiliary elastic members 19, when the auxiliary elastic members are in the non-stretched state but remain attached to the base sheet, is also shown in FIG. 2 for the same reason.

The dimension L1 is preferably 1 to 5 mm longer than the dimension L2. Consequently, it is unlikely that the auxiliary elastic members 19 might contract to a dimension smaller than the dimension L2, thereby preventing wrinkles from being formed in the panel 25 due to the contractile force of the contracting auxiliary elastic members 19. Alternatively, the dimension L1 may be substantially equal to the dimension L2 of the panel 25.

The ratio L3/L1 is in a range of 1-1.1.

If the ratio L3/L1 exceeds 1.1, a range within which the region of the base sheet 2 is stretchable and contractible would be smaller than a range within which the auxiliary elastic members 19 are stretchable and contractible and therefore the range within which the auxiliary elastic members 19 are stretchable and contractible could not be sufficiently utilized.

The auxiliary elastic members 19 are attached to the base sheet 2 as the auxiliary elastic members 19 are stretched preferably at a stretching ratio of 1.5 to 4.0. If the stretching ratio is less than 1.5, the range within which the base sheet 2 is stretchable and contractible could not be sufficiently utilized and the range within which the base sheet 2 is stretchable and contractible would be thereby restricted. Consequently, the article 1 cannot be widely adjusted to the size of the wearer's waist. If the ratio exceeds 4.0, there is an anxiety that the transversely opposite end portions 19a of the respective auxiliary elastic members 19 might come off the sheets 5, 6.

The ratio L3/L1 is calculated in accordance with the following procedures:
(1) The front or rear waist region having the auxiliary elastic members 19 is cut from the article 1 to obtain a sample sheet for measurement.
(2) Dimension L3 of a middle portion of the sample sheet defined between the end portions 19a where the auxiliary elastic members 19 are bonded to the base sheet is measured when the sample sheet as well as the auxiliary elastic member 19 are not stretched.
(3) After measurement of dimension L3, one or more of the auxiliary elastic members 19 is/are cut between their end portions 19a to obtain their intermediate portion or working section 19b. Then the intermediate portion or working section 19b is rinsed with a suitable organic solvent, such as toluene, to remove any adhesive residue. Thereafter, the rinsed working section 19b is dried and dimension L1 of working section 19b in a relaxed, non-stretched state is measured.
(4) Dimension L3 is divided by dimension L1 to calculate the ratio L3/L1.

In the front and rear waist regions 7, 9, the inner sheet 6 and the outer sheet 5 are joined together by means of a plurality of adhesive spots 20. These adhesive spots 20 are distributed between each pair of the adjacent auxiliary elastic members 19 at given intervals in the longitudinal direction as well as in the waist-circumferential direction. These adhesive spots 20 are provided in the form of dots and distributed in substantially entire area of the zone 17 of the front and rear waist regions 7, 9 occupied by both the panel 25 and auxiliary elastic members 19.

The adhesive spots 20 comprise an array of first adhesive spots 21 intermittently arranged in the longitudinal direction in a transversely middle zone of the panel 25, two arrays of second adhesive spots 22 intermittently arranged in the longitudinal direction on both sides of the array of first adhesive spots 21 and two arrays of third adhesive spots 23 intermittently arranged in the longitudinal direction in vicinities of the transversely opposite side edges 25b of the panel 25. Of the first and second adhesive spots 21, 22, the adhesive spots 21a, 22a at the uppermost positions of the front and rear waist regions 7, 9 are formed between the uppermost auxiliary elastic member 19c extending in the vicinities of the longitudinally opposite ends 25a of the panel 25 and these opposite ends of the panel 25. Of the third adhesive spots 23, the adhesive spots 23a at the uppermost positions of the front and rear waist regions 7, 9 are formed at cross-points of the longitudinally opposite ends 25a and the transversely opposite side edges 25b of the panel 25.

The number of the adhesive spots 20 arranged in the longitudinal direction is not limited to the number as illustrated. The pattern of the adhesive spots is not limited to the dot-pattern as illustrated but may be line-pattern or ribbon-pattern wherein each of the lines or ribbons extends in the waist-circumferential direction. The first and second adhesive dots are not essential so far as the outer sheet 5 and the inner sheet 6 are reliably joined together by means of the third adhesive spots 23.

The panel 25 comprises a liquid-pervious upper sheet 26 facing the wearer's body, a liquid-impervious lower sheet 27 facing away from the wearer's body and a liquid-absorbent core 28 interposed between the upper and lower sheets 26, 27 and secured to respective inner surfaces of these sheets 26, 27. The panel 25 presents a substantially rectangular planar shape and extends over the crotch region 8 of the base sheet 2 into the front and rear waist regions 7, 9. The panel 25 is provided in the vicinities of its opposite side edges 25b with a pair of substantially liquid-impervious side sheets 29.

In the panel 25, peripheral margins of the upper and lower sheets 26, 27 extending outward beyond the peripheral edge of the core 28 are overlaid and joined together. Over a substantially entire area of the panel 25 lying in the front and rear waist regions 7, 9 of the base sheet 2 is secured to the inner surface of the inner sheet 6 extending in the front and rear waist regions 7, 9 by means of the lower sheet 27.

Each of the side sheets 29 has a fixed side edge portion 29a secured to the panel 25 in the vicinities of the associated side edge 25b so as to extend in the longitudinal direction, a free side edge portion 29b extending parallel to the fixed side edge portion 29a in the longitudinal direction and longitudinally opposite fixed end portions 29c collapsed toward the transversely middle zone of the panel 25 and secured to the panel 25 in the vicinities of the respective end portions 25a of the panel 25 so as to be held in the collapsed state. The free side edge portion 29b is provided with an elastically stretchable member 30 attached thereto in a stretched state.

The core 28 comprises a mixture of fluff pulp and superabsorbent polymer particles or a mixture of fluff pulp, superabsorbent polymer particles and thermoplastic synthetic resin fibers, in both cases, compressed to a desired thickness. Thus the panel 25 has a stiffness higher than those of the inner sheet 6 and the outer sheet 5.

Preferably, the core 28 is entirely wrapped with a liquid-pervious sheet such as a tissue paper or a hydrophilic fibrous nonwoven fabric in order to prevent the core 28 from getting out of shape and/or to avoid falling off of the polymer particles. The polymer particles may be selected from the group consisting of starch-based polymer particles, cellulose-based polymer particles and synthetic polymer particles.

The elastic members 30 contract as the panel 25 curves in the longitudinal direction with the upper sheet 26 inside and thereupon the respective free side edge portions 29b of the side sheets 29 rise above the upper sheet 26 so as to form barriers adapted to prevent bodily discharges from leaking out beyond the opposite side edges 25b of the panel 25.

Joining of the inner and outer sheets 6, 5 to each other, attaching of the elastic members 15, 16, 19 to the inner and outer sheets 6, 5, joining of the inner sheet 6 and the lower sheet 27 to each other, joining of the upper and lower sheets 26, 27 to each other and securing of the core 28 to the upper and lower sheets 26, 27 are carried out using a hot melt adhesive (not shown).

In the article 1, each of the auxiliary elastic members 19 has its intermediate portion 19b secured neither to the inner sheet 6 nor to the outer sheet 5 and therefore so far as the intermediate portion 19b is concerned, contraction of the intermediate portion 19b, which constitutes a major part of the working section of the auxiliary elastic member, is not restricted by the presence of the adhesive. Consequently, it can be ensured that the region of the base sheet 2 which is coextensive with the working section of the auxiliary elastic members 19 can be contracted to a dimension L3 of about 1.0 to 1.1 times the natural or relaxed dimension L1 of the working sections of the auxiliary elastic members 19. In this way, the region of the base sheet 2 is stretchable and contractible within a substantially same range as the range within which the working sections of the auxiliary elastic members 19 are stretchable and contractible. As a result, the article 1 can be widely adjusted to the size of the wearer's waist.

In the article 1, the intermediate portions 19b of the respective auxiliary elastic members 19 are secured neither to the inner sheet 6 nor to the outer sheet 5, so the inner sheet 6 and the outer sheet 5 are not formed with a plurality of gathers except for the waist surrounding upper end portion 10 and the vicinities of the lateral margins 13 of the respective transversely opposite lateral zones 11. The absence of the gathers is effective to improve touch and appearance of these sheets 5, 6. In the region 17 of these sheets 5, 6 occupied by the panel 25, due to a stiffness of the panel 25, a contractile force of the auxiliary elastic members 19 is prevented from affecting the portions of the inner sheet 6 and the outer sheet 6 lying in the region 17 even when the auxiliary elastic members 19 contract in the waist-circumferential direction. Thus the outer sheet 5 is kept substantially flat and the illustration 18 of the bear cub displayed on this outer sheet 5 can be clearly recognized.

In the article 1, the dimension L1 of the working sections of the auxiliary elastic members 19 when the working sections are in a non-stretched state and are not attached to the base sheet 2 is 1 to 5 mm longer than the dimension L2 of the panel 25 defined between its transversely opposite side edges 25b in the waist-circumferential direction. With this dimensioning, the panel 25 is not formed with gathers or wrinkles due to the contractile force of the auxiliary elastic members 19. This is for the reason that the auxiliary elastic members 19 do not contract in the waist-circumferential direction to a dimension that may be smaller than the dimension L2 of the panel 25.

In the article 1, a plurality of adhesive spots 20 distributed between each pair of the adjacent auxiliary elastic members 19 serve to prevent the auxiliary elastic members 19 from shifting in the longitudinal direction. Furthermore, the article 1 is provided between the uppermost auxiliary elastic members 19c extending in the transverse direction in the vicinities of the longitudinally opposite ends 25a of the panel 25 and the respective longitudinally opposite ends 25a of the panel 25 with adhesive spots 21a, 22a, 23a. These adhesive spots 21a, 22a, 23a serve to prevent the uppermost auxiliary elastic members 19c from shifting outward beyond the longitudinally opposite ends 25a of the panel 25. In addition, the uppermost auxiliary elastic members 19c function to support the panel 25 in the vicinities of its longitudinally opposite ends 25a and thereby to prevent these opposite ends 25a of the panel 25 from protruding outward from the base sheet 2.

Figure 5:
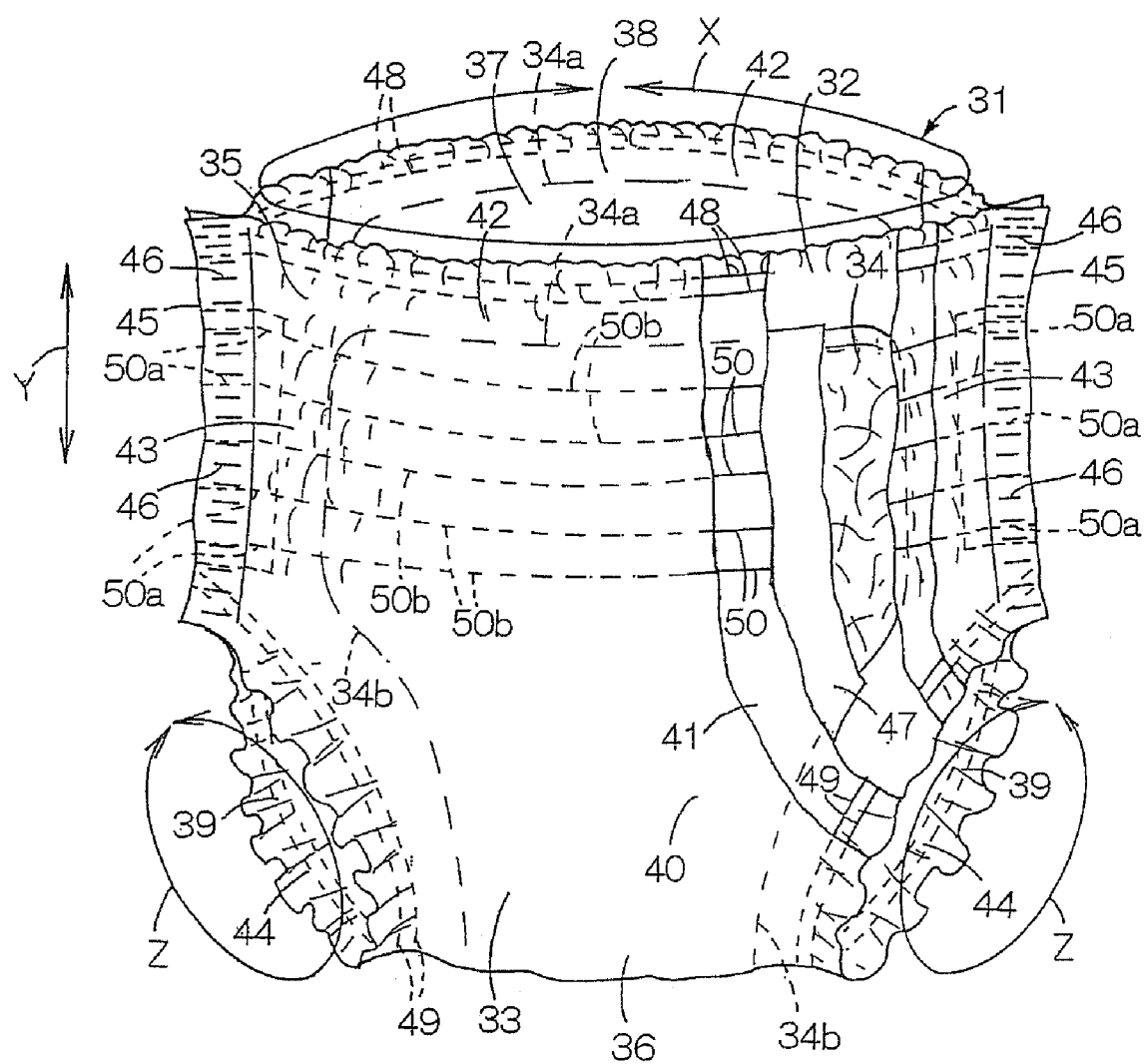
FIG. 5 is a partially cutaway perspective view showing another embodiment of the disposable wearing article according to the invention.
Figure 6:
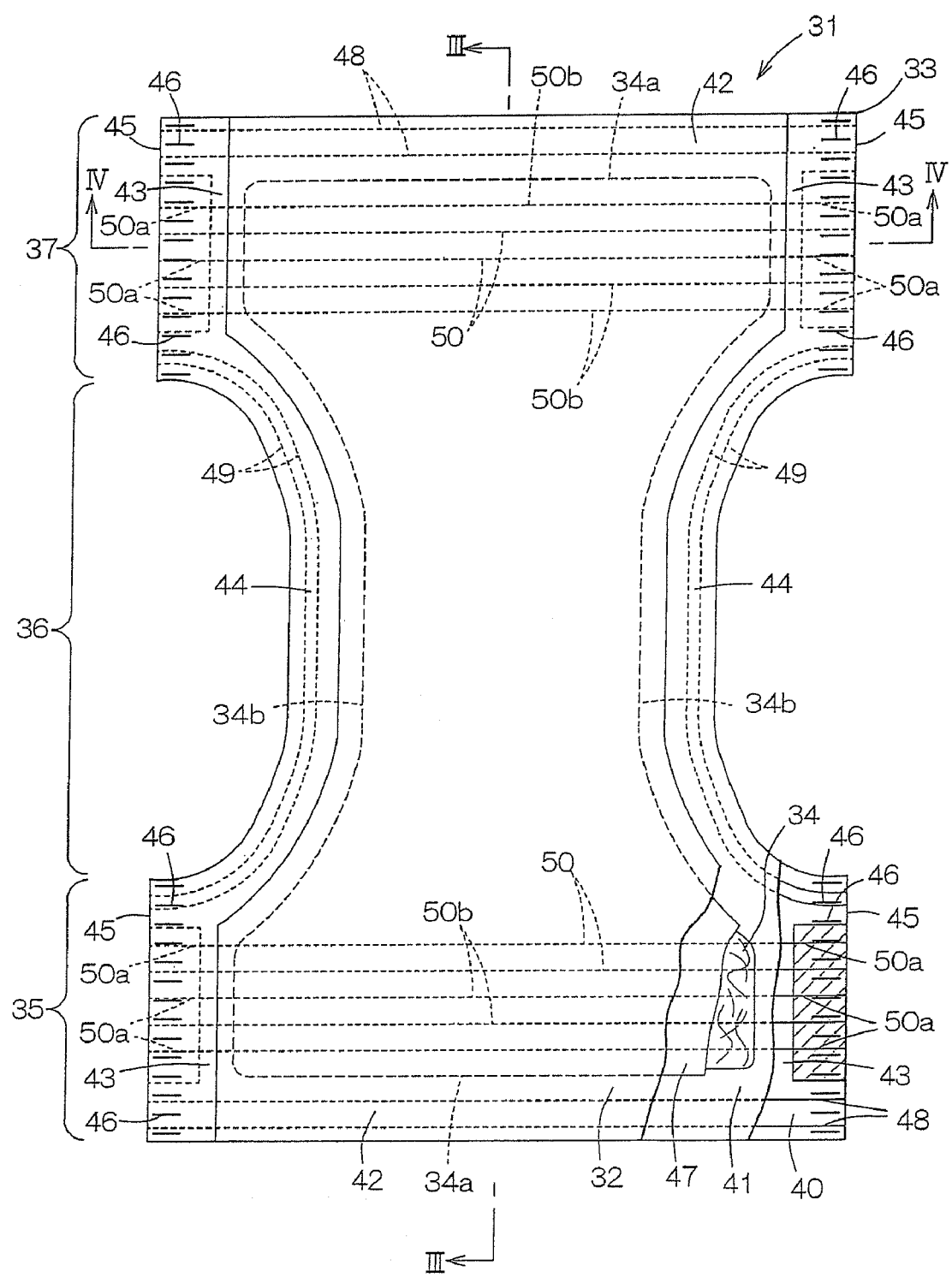
FIG. 6 is a developed plan view showing the article of FIG. 5 with the front and rear waist regions being disconnected from each other.
Figure 7:
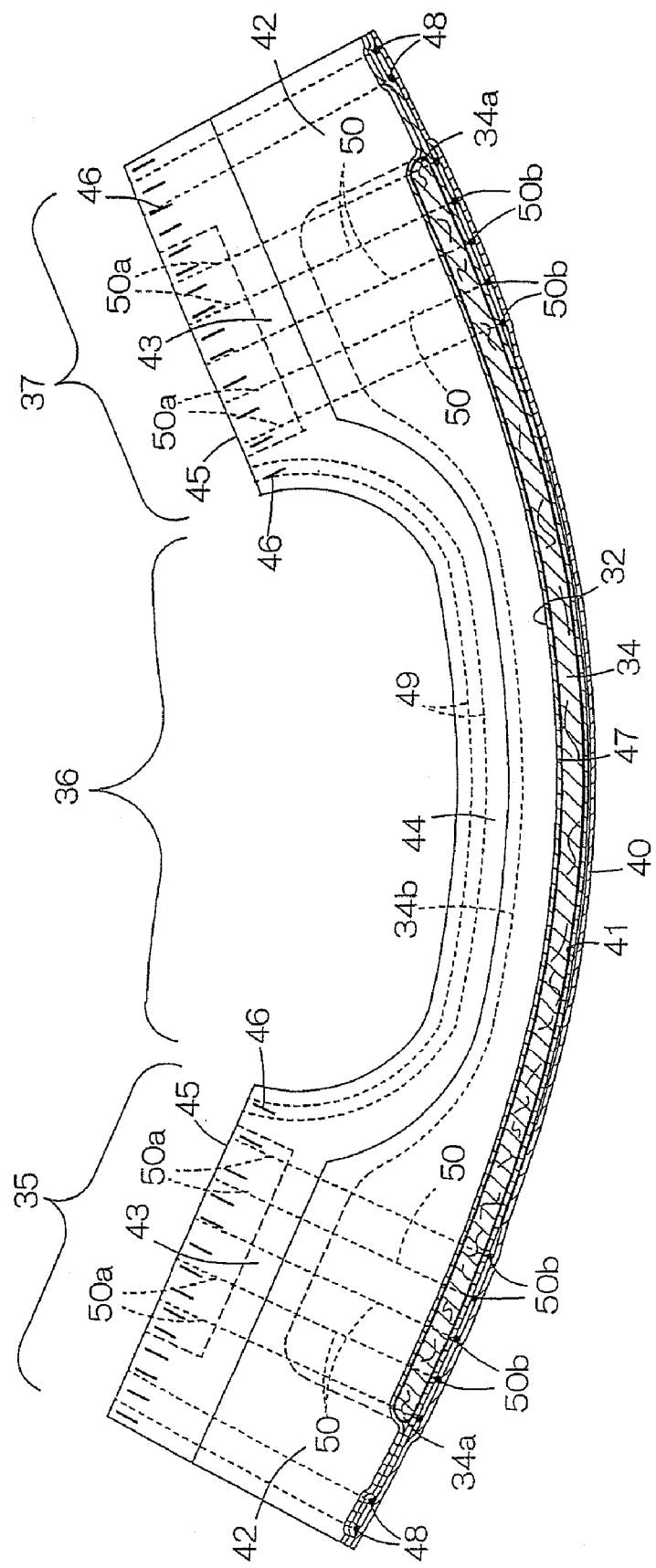
FIG. 7 is a sectional view taken along a line III-III in FIG. 6.
Figure 8:
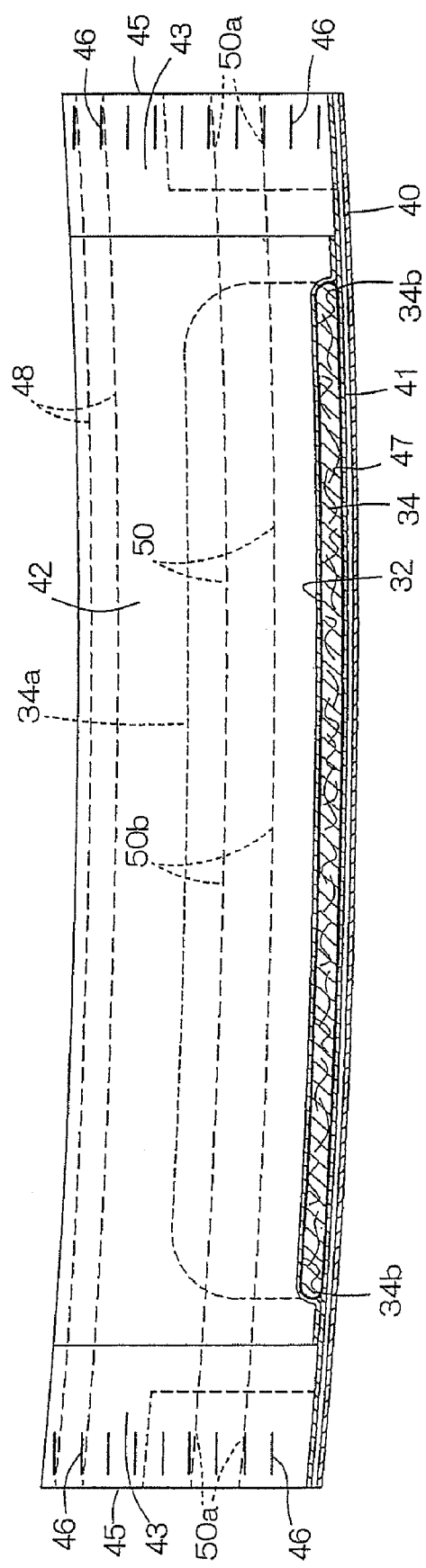
FIG. 8 is a sectional view taken along a line IV-IV in FIG. 6.

FIG. 5 is a partially cutaway perspective view showing a disposable wearing article 31 according to another embodiment of the invention, FIG. 6 is a developed plan view showing the article 31 of FIG. 5 with the front and rear transversely opposite lateral zones 43 disconnected from one another, FIG. 7 is a sectional view taken along a line III-III in FIG. 6, showing the article 31 as slightly curving and FIG. 8 is a sectional view taken along a line IV-IV in FIG. 6. In FIG. 5, the waist-circumferential direction is indicated by the arrow X, the longitudinal direction is indicated by the arrow Y and the leg-circumferential direction is indicated by the arrow Y.

The article 31 comprises a liquid-pervious topsheet 32 facing the wearer's body, a liquid-impervious backsheet 33 (base sheet) and a liquid-absorbent core 34 (liquid-absorbent panel). The article 1 has front and rear waist regions 35, 37 and a crotch region 36 lying between these front and rear waist regions 35, 37.

The article 31 has a waist surrounding upper end portion 42 lying outside longitudinally opposite ends 34a of the core 34, transversely opposite lateral zones 43 lying outside transversely opposite side edges 34b of the core 34 and leg-holes' peripheral portions 44 lying outside the respective side edges 34b of the core 34. In the article 31, lateral margins 45 of the respective transversely opposite lateral zones 43 are overlaid and joined together by means of a plurality of heat-sealing sites 46 intermittently arranged in the longitudinal direction in vicinities of the respective lateral margins 45. The article 31 has a waist-hole 38 and a pair of leg-holes 39.

The backsheet 33 comprises an inner sheet 41 (first sheet) facing the core 34 and an outer sheet 40 (second sheet) lying outside the inner sheet 41. The outer sheet 40 and the inner sheet 41 are overlaid and joined together along the waist surrounding upper end portion 42, in the vicinities of the lateral margins 45 of the transversely opposite lateral zones 43 and along the leg-holes' peripheral portions 44.

The core 34 extends over the crotch region 36 into the front and rear waist regions 35, 37. Similarly to the core 28 shown in FIG. 1, the core 34 has a stiffness higher than those of the topsheet 32, the inner sheet 41 and the outer sheet 40. The core 34 is entirely wrapped with a tissue paper 47 and has the lower surface which is, substantially over its entire area, secured to the inner surface of the inner sheet 41 extending in the front waist region 35, the crotch region 36 and the rear waist region 37 with the tissue paper 47 therebetween.

A dimension of the topsheet 32 as measured in the waist-circumferential direction is smaller than those of the inner sheet 41 and the outer sheet 40 as measured in the waist-circumferential direction. A peripheral portion of the topsheet 32 extending outward beyond the peripheral edge of the core 34 is secured to the inner surface of the inner sheet 41.

A plurality of waist surrounding elastic members 48 extending in the waist-circumferential direction are attached to the waist surrounding upper end portion 42 so as to be contractible in the waist-circumferential direction. Similarly, a plurality of leg surrounding elastic members 49 extending in the leg-circumferential direction are attached to the respective leg-holes' peripheral portions 44 so as to be contractible in the leg-circumferential direction. Both the waist surrounding elastic members 48 and the leg surrounding elastic members 49 are interposed between the inner sheet 41 and the outer sheet 40 and secured to the sheets 40, 41.

The front and rear waist regions 35, 37 are provided with a plurality of auxiliary elastic members 50 extending in the waist-circumferential direction across the core 34 so as to be contractible in the waist-circumferential direction. These auxiliary elastic members 50 are interposed between the inner sheet 41 and the outer sheet 40 and arranged between the waist surrounding elastic members 48 and the leg-holes 39 so that the auxiliary elastic members 50 adjacent to each other are spaced apart from each other by a given dimension in the longitudinal direction. Each of the auxiliary elastic members 50 has transversely opposite end portions 50a lying in the vicinities of the lateral margins 45 of the respective transversely opposite lateral zones 43 and secured to the inner sheet 41 and the outer sheet 40 and an intermediate portion 50b lying between the opposite end portions 50a and let free from both the outer sheet 40 and the inner sheet 41.

Each of the auxiliary elastic members 50 similarly to auxiliary elastic members 19 has a working section which, when it is in a non-stretched state and is not attached to the backsheet 33, has dimension L1 preferably substantially equal to a dimension of the core 34, or 1 to 5 mm longer than the dimension of the core 34 as measured in the waist-circumferential direction. Like article 1, backsheet 33 has a region coextensive with the working section of the auxiliary elastic members 50 which has a non-stretched dimension similar to dimension L3 of FIG. 2. A ratio L3/L1 in this embodiment is preferably in a range of 1.0 to 1.1 as measured in the waist-circumferential direction. The auxiliary elastic members 50 are attached to the backsheet 33 as these auxiliary elastic members 50 are stretched preferably at 1.5 to 4.0 times its original length. Joining of the inner sheet 41 and the outer sheets 40 to each other, attaching of the elastic members 48, 49, 50 to the inner sheet 41 and the outer sheets 40, and securing of the topsheet 32 and the core 34 to the inner sheet 41 are carried out using a hot melt adhesive (not shown). The article 31 can be widely adjusted to the size of the wearer's waist as discussed above with respect to article 1.

In the article 31, the outer and inner sheets 40, 41 extending in the front and rear waist regions 35, 37 undulate gently as the auxiliary elastic members 50 contract in the waist-circumferential direction. However, it is not likely that the outer and inner sheets 40, 41 might be formed with a plurality of fine gathers except for the waist surrounding upper end portion 42, the vicinities of the lateral margins 45 of the lateral zones 43 and the peripheral portions 44 of the leg-hole 39. This is for the reason that the intermediate portions 50b of the respective auxiliary elastic members 50 are not secured to the outer and inner sheets 40, 41. Furthermore, it is not likely that the core 34 might be formed with wrinkles when the auxiliary elastic members 50 contract, as discussed with respect to article 1.

A stock material for the outer sheet 5, 40, the inner sheet 6, 41 and the lower sheet 27 may be selected from the group consisting of a substantially liquid-impervious hydrophobic fibrous nonwoven fabric, a breathable but liquid-impervious thermoplastic film, composite nonwoven fabric comprising two or more layers of hydrophobic fibrous nonwoven fabric laminated upon one another and a composite sheet comprising a hydrophobic fibrous nonwoven fabric and a breathable but liquid-impervious plastic film placed upon each other. A stock material for the upper sheet 26 and the topsheet 32 may be selected from the group consisting of a fibrous nonwoven fabric treated to be hydrophilic, a thermoplastic film having a plurality of perforations and a hydrophobic fibrous nonwoven fabric.

The nonwoven fabric may be selected from the group consisting of those obtained by spun lace-, needle punch-, melt blown-, thermal bond-, spun bond-, chemical bond- and air-through-processes. Component fibers of the nonwoven fabric may be selected from the group consisting of polyolefine-, polyester- and polyamide-based fibers and core-and-sheath type or side-by-side type conjugated fibers of polyethylene/polypropylene and polyethylene/polyester.

In the disposable wearing article according to the invention except for the waist surrounding upper end portion, the vicinities of the lateral margins of the respective lateral zones and the peripheral portions of the leg-hole, there is no possibility that the base sheet might be formed with a plurality of fine gathers. Thus not only touch but also appearance of the base sheet can be improved.

With the article according to the disclosed embodiment in which the first and second sheets are joined together by means of a plurality of bonding spots each formed between each pair of the auxiliary elastic members adjacent to each other so as to be arranged in the longitudinal direction, there is no anxiety that the auxiliary elastic members might shift in the longitudinal direction in the front and rear waist regions.

In the article according to the disclosed embodiment, it is not likely that the panel might be formed with wrinkles due to the contractile force of the auxiliary elastic members.

The invention claimed is:
1. A pull-on disposable wearing article, comprising:
 a base sheet defining a front waist region, a rear waist region and a crotch region extending between said front and rear waist regions;
 a liquid-absorbent panel attached to an inner side of said base sheet so as to extend over said crotch region and into said front and rear waist regions;

said base sheet having waist surroundable upper end portions lying outside longitudinally opposite ends of said panel and transversely opposite lateral zones lying outside transversely opposite side edges of said panel, wherein said transversely opposite lateral zones are connected to each other at bonding sites disposed longitudinally along lateral margins of said transversely opposite lateral zones to define a waist-hole and a pair of leg-holes;

waist surroundable elastic members extending in a waist-circumferential direction along said waist surroundable upper end portions;

a plurality of auxiliary elastic members located between said waist surroundable elastic members and said leg-holes in at least one of said front and rear waist regions, each of said auxiliary elastic members having a working section extending in the waist-circumferential direction between inner ends of the bonding sites;

wherein when each of said auxiliary elastic members is in a relaxed, non-stretched state and is not attached to said base sheet, the working section of said auxiliary elastic member has a first dimension as measured in said waist-circumferential direction;

said panel in said at least one of said front and rear waist regions has a second dimension as measured in said waist-circumferential direction between said transversely opposite side edges of said panel; said first dimension is substantially equal to or longer than said second dimension;

said base sheet has a region coextensive, in the waist-circumferential direction, with the working sections of said auxiliary elastic members, said region also extending between the inner ends of said bonding sites;

when said auxiliary elastic members are in a non-stretched state and remain attached to said base sheet, said region of said base sheet has a third dimension in the waist-circumferential direction; and a ratio of the third dimension to the first dimension is in a range of 1.0 to 1.1.

2. The wearing article according to claim 1, wherein said base sheet comprises first and second sheets joined to each other, and each of said auxiliary elastic members is positioned between said first and second sheets and has longitudinal opposite end portions lying in vicinities of said lateral margins of said transversely opposite lateral zones and secured to at least one of said first and second sheets of said base sheet, and an intermediate portion contiguous to, extending between and connecting said opposite end portions, said intermediate portion being directly bonded neither to the first sheet nor to the second sheet of said base sheet and defining said working portion.

3. The wearing article according to claim 1, wherein each of said auxiliary elastic members is stretched 1.5 to 4.0 times its original length while being bonded to said base sheet.

4. The wearing article according to claim 2, further comprising a plurality of joining spots joining said first and second sheets together, wherein at least one of said joining spots is positioned between each pair of adjacent said auxiliary elastic members; and all said joining spots are positioned between said transversely opposite side edges of said panel.

5. The wearing article according to claim 4, wherein said joining spots are distributed at regular intervals between said transversely opposite side edges of said panel; and each of said joining spots is positioned adjacent at least one of said auxiliary elastic members.

\* \* \* \* \*